US006890553B1

(12) United States Patent
Sun et al.

(10) Patent No.: US 6,890,553 B1
(45) Date of Patent: May 10, 2005

(54) EXOTHERMIC TOPICAL DELIVERY DEVICE

(75) Inventors: Ying Sun, Somerville, NJ (US); Ralph W. Oakeson, Racine, WI (US); Stephen J. Wisniewski, Doylestown, PA (US); Jonas C. T. Wang, West Windsor, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 09/612,357

(22) Filed: Jul. 7, 2000

Related U.S. Application Data

(60) Provisional application No. 60/142,757, filed on Jul. 8, 1999.

(51) Int. Cl.$^7$ ................................................ A61K 9/70
(52) U.S. Cl. ...................... 424/449; 424/400; 424/443; 424/447; 424/448; 602/41; 602/46
(58) Field of Search ......................... 424/449, 448, 424/447, 443, 402, 400; 602/41, 46

(56) References Cited

U.S. PATENT DOCUMENTS

| | | |
|---|---|---|
| 2,857,356 A | 10/1958 | Goodwin |
| 3,315,665 A | 4/1967 | MacLeod |
| 3,950,158 A | 4/1976 | Gossett |
| 3,964,482 A | 6/1976 | Gerstel et al. |
| 4,039,707 A | 8/1977 | O'Malley |
| 4,114,591 A | 9/1978 | Nakagawa |
| 4,230,105 A | 10/1980 | Harwood |
| 4,406,658 A | 9/1983 | Lattin et al. |
| 4,655,766 A | 4/1987 | Theeuwes et al. |
| 4,655,767 A | 4/1987 | Woodard et al. |
| 4,685,911 A | 8/1987 | Konno et al. |
| 4,747,841 A | 5/1988 | Kuratomi et al. |
| 4,767,402 A | 8/1988 | Kost et al. |

(Continued)

FOREIGN PATENT DOCUMENTS

| | | |
|---|---|---|
| DE | 195 25 607 A1 | 1/1997 |
| EP | 0 429 842 A2 | 6/1991 |
| GB | 2303208 | 12/1997 |
| WO | 86/07269 A1 | 12/1986 |
| WO | 92/07618 A1 | 5/1992 |
| WO | 93/17754 A1 | 9/1993 |
| WO | 94/23777 A1 | 10/1994 |
| WO | 95/30410 A3 | 11/1995 |
| WO | 96/17648 A1 | 11/1995 |
| WO | 96/00110 A1 | 1/1996 |
| WO | 96/37256 A1 | 11/1996 |
| WO | 97/04832 | 2/1997 |
| WO | 97/12644 A1 | 4/1997 |
| WO | 97/48440 | 12/1997 |
| WO | 97/48441 A1 | 12/1997 |
| WO | 97/48442 A1 | 12/1997 |
| WO | 98/11937 A1 | 3/1998 |
| WO | 98/28037 A1 | 7/1998 |
| WO | 98/28038 A1 | 7/1998 |
| WO | 98/29134 | 7/1998 |
| WO | 98/46124 A1 | 10/1998 |

OTHER PUBLICATIONS

Sun, Y. Skin Absorption Enhancement by Physical Means: Heat, Ultrasound, and Electricity. Transdermal and Topical Drug Delivery Systems. (1997) 327–355.

(Continued)

*Primary Examiner*—Thurman K. Page
*Assistant Examiner*—Konata M. George

(57) ABSTRACT

The present invention relates to an exothermic device for topically delivering an active agent comprising a liquid reservoir comprising water, a heating element comprising an oxidizable material, an oxygen-permeable outer-layer, an active agent, and a water-impermeable layer, wherein upon the rupturing of the liquid reservoir, the water contacts the heating element and the oxygen to create and exothermic reaction.

19 Claims, 1 Drawing Sheet

U.S. PATENT DOCUMENTS

| | | |
|---|---|---|
| 4,790,824 A | 12/1988 | Morrow et al. |
| 4,898,592 A | 2/1990 | Latzke et al. |
| 4,898,920 A | 2/1990 | Lee et al. |
| 4,925,671 A | 5/1990 | Abber |
| 4,927,408 A | 5/1990 | Haak et al. |
| 4,963,360 A | 10/1990 | Argaud |
| 4,994,260 A | 2/1991 | Kallstrand et al. |
| 5,013,293 A | 5/1991 | Sibalis |
| 5,036,861 A | 8/1991 | Sembrowich et al. |
| 5,042,975 A | 8/1991 | Chien et al. |
| 5,135,478 A | 8/1992 | Sibalis |
| 5,147,916 A | 9/1992 | Sweet |
| 5,156,591 A | 10/1992 | Gross et al. |
| 5,162,410 A | 11/1992 | Sweet |
| 5,186,938 A | 2/1993 | Sablotsky et al. |
| 5,213,568 A | 5/1993 | Lattin et al. |
| 5,224,927 A | 7/1993 | Tapper |
| 5,232,702 A | 8/1993 | Pfister et al. |
| 5,250,023 A | 10/1993 | Lee et al. |
| 5,252,334 A | 10/1993 | Chiang et al. |
| 5,279,543 A | 1/1994 | Glikfeld et al. |
| 5,279,544 A | 1/1994 | Gross et al. |
| 5,320,607 A | 6/1994 | Ishibashi |
| 5,344,394 A | 9/1994 | Gyory et al. |
| 5,362,307 A | 11/1994 | Guy et al. |
| 5,386,837 A | 2/1995 | Sterzer |
| 5,399,163 A | 3/1995 | Peterson et al. |
| 5,438,984 A | 8/1995 | Schoendorfer |
| 5,441,490 A | 8/1995 | Svedman |
| 5,527,288 A | 6/1996 | Gross et al. |
| 5,533,971 A | 7/1996 | Phipps |
| 5,540,669 A | 7/1996 | Sage, Jr. et al. |
| 5,573,778 A | 11/1996 | Therriault et al. |
| 5,582,586 A | 12/1996 | Tachibana et al. |
| 5,591,124 A | 1/1997 | Phipps |
| 5,614,502 A | 3/1997 | Flotte et al. |
| 5,636,632 A | 6/1997 | Bommannan et al. |
| 5,658,583 A | 8/1997 | Zhang et al. |
| 5,658,892 A | 8/1997 | Flotte et al. |
| 5,662,624 A | 9/1997 | Sundstrom et al. |
| 5,667,491 A | 9/1997 | Pliquett et al. |
| 5,718,955 A | 2/1998 | McGuire et al. |
| 5,780,050 A | 7/1998 | Jain et al. |
| 5,853,383 A | 12/1998 | Murdock |
| 5,857,992 A | 1/1999 | Haak et al. |
| 5,885,211 A | 3/1999 | Eppstein et al. |
| 6,050,988 A | 4/2000 | Zuck |
| 6,083,196 A | 7/2000 | Trautman et al. |
| 6,104,952 A | 8/2000 | Tudetdal |
| 6,245,347 B1 * | 6/2001 | Zhang et al. ............... 424/449 |

OTHER PUBLICATIONS

Buyuktimkin N., Buyuktimkin S. Chemical Means of Transdermal Drug Permeation Enhancement. Transdermal and Topical Drug Delivery Systems. (1997) 357–475.

Sun Y., Liu J.C., Xue H. Important Parameters Affecting Iontophoretic Transdermal Delivery of Insulin. Proceed. Intern. Symp. Control. Rel. Bioact. Mater., 17, Controlled Release Society, Inc. (1990) 202–203.

Roberts M. Lai P., Cross S., Yoshida N. Solute Structure as a Determinant of Iontophoretic Transport. Mechanisms of Transdermal Drug Delivery. (1997) 291–349.

PCT Search Report Dated Oct. 25, 2000 of International Application No. PCT/US 00/18650.

* cited by examiner

EXOTHERMIC TOPICAL DELIVERY DEVICE

CROSS-REFERENCE TO RELATED APPLICATION

This application claims the benefit of provisional application Ser. No.: 60/142,757 filed on Jul. 8, 1999.

FIELD OF THE INVENTION

The present invention relates to a delivery device comprising a heating element and the use thereof for enhanced topical and transdermal delivery of active agents.

BACKGROUND OF THE INVENTION

To Topical dosage forms have been widely prescribed for decades in the treatment of systemic diseases and local conditions such as those involved with the skin and underlying tissues. Certain drugs are relatively easy to be delivered via the transdermal or transmucosal route because they can easily permeate through the skin or mucosal membrane at a high potency. Permeation of the drug across the skin or mucosal membrane from a transdermal patch or a mucosal patch is a result of the chemical potential gradient across the skin or mucosal membrane. Examples of these drugs include nitroglycerin, scopolamine, nicotine, hydrocortisone, betamethasone, benzocaine, and lidocaine.

Most drugs and biological active ingredients, however, cannot readily penetrate through the skin or mucosal membrane. Therefore, to increase skin permeation of these drugs, various chemical and physical permeation enhancing methods have been employed. Chemical permeation enhancing agents may be applied typically to increase transdermal delivery of drugs. Generally, chemical permeation enhancing agents are cost effective and safe. An extensive review of chemical penetration enhancing agents is reported in Buyuktimkin et al., "Chemical Means of Transdermal Drug Permeation Enhancement", *Transdermal and Topical Drug Delivery Systems*, Interpharm Press, Inc., 1997, pages 357–475. One major disadvantage associated with chemical penetration enhancers is potential skin irritation.

Physical penetration enhancing methods can also be used to improve transdermal drug delivery. The energy forms employed for this purpose include electricity (e.g., iontophoresis), ultrasound (e.g., phonophoresis) and thermal energy (e.g., heat-assisted delivery), which are reviewed by Sun, "Skin Absorption Enhancement by Physical Means: Heat, Ultrasound, and Electricity", *Transdennal and Topical Drug Delivery Systems*, Interpharm Press, Inc., 1997, pages 327–355.

U.S. Pat. No. 4,898,592 relates to a device for the application of heated transdermally absorbable active substances that includes a carrier impregnated with the transdermally absorbable active substance and a support. The support is a laminate made up of one or more polymeric layers and optionally includes a heat conductive element. This heat conductive element is used for distribution of the patient's body heat such that absorption of the active substance is enhanced. This device, however, has no heat-generating element or function. The use of only a heat conductive element to distribute body heat, however, is not an efficient or reliable method of enhancing transdermal absorption by heating since the amount of body heat given off by a patient can vary depending on the ambient air temperature and the physical conditions of the patient.

U.S. Pat. No. 4,747,841 discloses a method and apparatus for "moxibustion" using a heat-generating element to heat and vaporize "moxall" for treatment of a patient's skin without leaving burn scars. The objective of this method and apparatus, however, is to achieve heat stimulation of the body and not to increase skin permeability.

U.S. Pat. No. 4,230,105 discloses a bandage with a drug and a heat-generating substance, preferably intermixed, to enhance the rate of absorption of the drug by the user's skin. Separate drug and heat-generating generation substance layers are also disclosed. water must be applied to the bandage to activate the heating substance to release solvation heat. Because the exothermal reaction during the hydration of the electrolytes disclosed in this patent only produces a transient low level of heat, it cannot be effectively used as a penetration enhancing method over a long period of time (e.g., for up to one day). Further, the speed of the hydration process is rather difficult to control.

U.S. Pat. No. 4,685,911 discloses a skin patch including a drug component and an optional heating element for melting the drug-containing formulation if the user's body temperature is inadequate to do so. The heating element is not substantially co-extensive with the drug reservoir, the latter being quite thick and, thus, not susceptible to even and rapid onset of heating. There is also no description on how to control the exothermic reaction to have prolonged and even heating.

U.S. Pat. No. 4,963,360 describes an exothermic device having a carrier layer, which comprises a medicinal component, and an exothermic layer, which develops heat when exposed to the air to enhance absorption of the medicinal component through the skin. The exothermic layer comprises a mixture of iron powder, carbon powder, salts (i.e., sodium chloride and aluminum chloride), and water. There is a base sheet to separate the exothermic layer from the medicinal layer in two separate chambers, and an air-permeable film that covers the exothermic layer.

U.S. Pat. No. 5,658,583 describes a heat-generating generation apparatus for improved dermal permeation of pharmaceuticals. The apparatus includes a thin drug formulation reservoir and a heat-generating chamber separated by a non-permeable wall. The drug formulation reservoir houses a predetermined amount of a formulation containing pharmaceutical agents. The heat-generating/temperature-regulating chamber includes a heat-generating medium consisting of carbon, iron, water and/or salt which is activated upon contact with oxygen in the air. The structure of the apparatus also includes a cover that is not permeable to air, but is perforated with holes to regulate the contact between the heat-generating medium and air, thereby, controlling the heating temperature.

U.S. Pat. No. 5,662,624 describes a heat dressing for treatment of skin areas comprising a heat generating unit and a liquid-absorbing adhesive layer that, prior to use, is coated with a release layer. The adhesive layer is preferably made of a hydro-colloidal material and may optionally contain one or more medicaments or may be coated with alginate fiber mats. The heat-generating unit generates heat preferably by means of galvanic or chemical energy, and the heat dressing may further comprise elements for controlling the heat development and/or the surface temperature. Such elements include a cover sheet for the heat-generating unit that is perforated for air passage, is covered by a heat-reflecting foil, or is a polymeric foam to better retain the heat.

The present invention relates to an exothermic delivery device for administration of active agents through a barrier membrane (e.g., the skin, mucosal membrane, or nails of a human). The advantages of the present device include:

better-controlled heatgeneration process, and consequently, an improved delivery profile of the active agents; an easier control on the product stability during storage; and simple manufacturing process for the device.

SUMMARY OF THE INVENTION

In one aspect, the invention features An exothermic device for topically delivering an active agent, the device comprising: (a) a liquid reservoir, the reservoir comprising water; (b) a heating element, the heating element comprising an oxidizable material and where the heating element is in communication with the liquid reservoir; (c) an oxygen-permeable outer-layer, wherein the oxygen-permeable layer is in communication with the heating element, permits oxygen from the environment to contact the heating element, and substantially inhibits the permeation of water from the heating element into the environment; (d) an active agent; and (e) a water-impermeable layer, wherein the water-impermeable layer separates the heating element and the active agent; wherein upon the rupturing of the liquid reservoir, the water contacts the hating element and the oxygen to create and exothermic reaction.

In another aspect, the invention features a method of topically delivering an active agent to a mammal (e.g., a human), the method comprising attaching the device of the present invention to a barrier membrane (e.g., the skin, mucosal membrane, or nails) of the mammal.

Other features and advantages of the present invention will be apparent from the detailed description of the invention and from the claims.

DETAILED DESCRIPTION OF THE INVENTION

Figure 1:
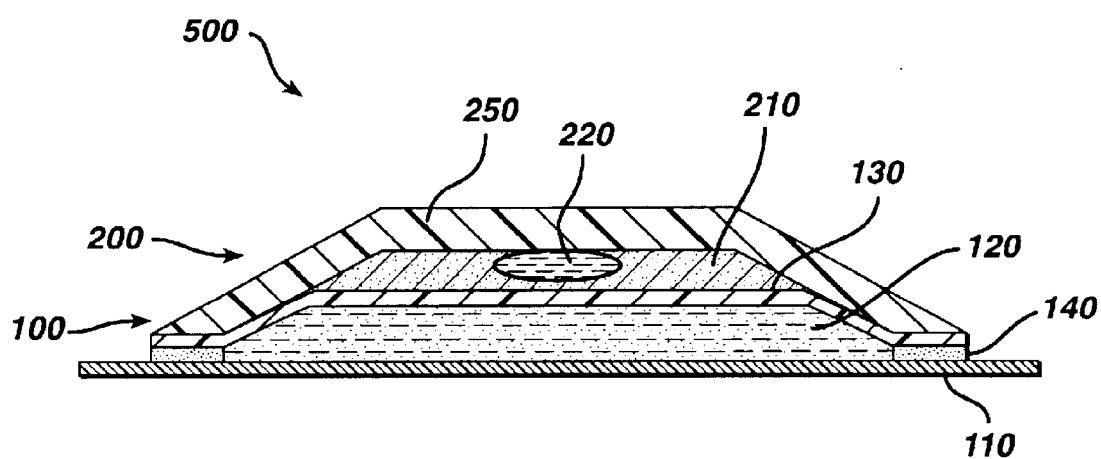
FIG. 1 is a cross-sectional view of an exothermic delivery device for active agents showing one embodiment of the present invention.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a novel exothermic delivery device of active agent(s) to barrier membranes, such as human skin, muc/osal membrane (e.g., buccal membrane), and nails. The exothermic delivery device of the present invention does not suffer from many of the disadvantages of the existing apparatuses previously described. For example, all of the prior devices described above control the heat generation process by the mere regulation of oxygen availability to the oxidation reaction in the heat-generating medium, e.g., by covering the heat-generating medium with a perforated membrane. The size and number of the thermo-regulating holes on the permeable membrane, thus, determines the amount of oxygen that reaches the oxidizable medium.

The disadvantages of such an approach include: (a) the requirement for a strict control of a non-oxygen environment during the manufacturing process since an extremely oxidizable mixture has to be processed and packaged into each apparatus and (b) a strict requirement on the type of packaging material for the finished product since any leakage of atmospheric oxygen will not only prematurely consume the heat-generating medium, but also stimulate the decomposition of the drug substances as a result of the elevated temperature.

The heating element of the present invention cannot react until activated by the user as the device includes a separate liquid reservoir containing the water requisite for the exothermic reaction. As represented schematically in FIG. 1, the device 500 consists of active-agent unit 100 and a heating unit 200. The active agent unit 100 comprises an active agent-containing layer 120 and a water-impermeable layer 130 separating the active agent-containing layer 120 from the heating unit 200. The water-impermeable layer 130 is impermeable to the active agent in the active agent-containing layer 120 and any solid or liquid material in the heating unit 200.

The water-impermeable layer may be made of flexible material well-known in the art to be impermeable to water, e.g., polymers such as polyethylene, polypropylene, polyvinyl acetate, polyurethane, silicone rubber, and polyvinyl chloride.

The active agent-containing layer 120 comprises the active agent. The active agent-containing layer may further comprise a carrier compatible with the active agent, such as a hydrogel, an adhesive, a semi-solid carrier such as a cream, lotion, ointment, or liquid crystal. It may also comprise a solid supporting matrix (e.g., a gauze or sponge-like foam materials). Active agents such as drugs and nutrients and other biologically active agents are incorporated into the carrier within the active agent-containing layer 120, e.g., as dissolved molecules and ions, dispersed solid particles, or liquid droplets.

As used herein, the term "active agents" refers drugs and nutrients for local treatment or systemic treatment (e.g., a therapeutic or cosmetic benefit). Typically these agent include, but are not limited to, antihypertensive drugs (e.g., clonidine), analgesic drugs (e.g. fentanyl, ibuprofen, benzocaine, and lidocaine), drugs to treat coronary artery diseases (e.g., nitroglycerin, low molecular weight heparin), drugs to assist wound healing (e.g., PDGF), antimicrobial agents, antipsoriatic agents, anti-inflammatory agents, anti-cancer agents, endocrine and metabolic medication (e.g., testosterone, estradiol), neurologic medications, medication for cessation of chemical additions (e.g., nicotine), motion sickness (scopolamine), and protein and peptide drugs. Most of these agents are known and may be used at concentrations and for durations of time which have proved effective against their respective disease states. These therapeutic agents are described in "Goodman & Gilman's The Pharmcological Basis of Therapeutics", $9^{th}$ Edition by J. G. Hardman,et al., (McGraw-Hill Companies, 1996).

Other active agents include those commonly used as for topical treatment and in cosmetic treatment of skin tissues, such as salicylic acid, benzoyl peroxide, resorcinol, resorcinol monoacetate, and sulfur for acne, topical antibiotics for wounds, topical antifungal drugs to treat fungal infections of the skin and nails, and antipsoriatic drugs to treat psoriatic lesions of the skin and psoriatic nails. Examples of antifungal drugs include but are not limited to miconazole, econazole, ketoconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts. In one embodiement, the antifungal drugs are an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline hydrochloride and tetrachycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts.

Examples of antipsoriatic drugs include but are not limited to corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone venerate, hydrocortisone butyrate, aclometasone dipropionte, flurandrenolide, mometasone furoate, methylprednisolone acetate), methotrexate, cyclosporine, calcipotriene and anthraline.

Additional examples of active agents include but are not limited to minoxidil, minoxidil sulfate, retinoids, cysteine and acetyl cysteine, methionine, glutathione, biotin, finasteride and ethocyn, as well as pharmaceutically acceptable salts of these compounds.

The active agents in the present invention may provide certain benefits to the superficial tissues such as the skin, for example: anti-aging, wrinkle removal, depigmentation (e.g., removal of "age spot"), skin tone improvement. The exothermic device in the present invention may be made into facial and body masks of various shape and size to fit the contours of the anatomic locations. The materials for the each layer of the multi-laminate device is preferably pliant for this purpose. The examples of active agents for aforementioned purposes include, but are not limited to: amino acids, and their derivatives, biotin, vitamins, vitamin B complex: thiamine, nicotinic acid, biotin, pantothenic acid, choline riboflavin, vitamin $B_6$, vitamin $B_{12}$, pyridoxine, inositol, carnitine; ascorbic acid, ascorbyl palmitate, vitamin A, vitamin K, vitamin E, vitamin D, cysteine and N-acetyl cysteine, herbal extracts, and their derivatives; soy extracts, calcium pantothenate, calcium carbonate, and calcium gluconate. Examples of retinoids include but not limited to retinol (Vitamin A alcohol), retinal (Vitamin A aldehyde), retinyl acetate, etinyl palmitate, retinoic cid, 9-cis-retinoic acid and 13-cis-retinoic acid. Examples of flavonoids include but not limited to naringenin, quercetin, catechins (e.g., epigallocatechin gallate), theaflavins, robustaflavone, hinokiflavone, amentoflavone, agathisflavone, volkensiflavone, morelloflavone, rhusflavanone, and succedangeaflavanone.

The exothermic device 500 is suitable to be used deliver agents to remove corn, callus, ingrown toe nails, and diseased nails from infections. The active agents for such a treatment include, but are not limited to, salicylic acid, urea, sodium sulfide, tannic acid, salts of thioglycolic acid, cysteine and acetyl cysteine.

The exothermic device is also suitable to be used deliver agents such as salicylic acid and benzoyl peroxide to treat acne.

The exothermic device is also suitable to be used deliver agents such as retinoids and herbal and soy extracts to provide anti-aging benefits including wrinkle and age-spot removal and improving skin tone.

In another embodiment, the device does not comprise an active agent-containing layer (e.g., it is used to help promote wound healing as a bandage).

The device 500 comprises a pressure-sensitive adhesive 140 to assist affixing the device 500 to the user's barrier membrane (e.g., dermal or mucosal barrier membrane). The adhesive in the adhesive layer may be a polymeric, pressure sensitive and nonconductive and remains adherent even after prolonged exposure to water. Typically, the adhesive has a broad working temperature range. Suitable adhesive materials include, but are not limited to, silicones, polyisobutylenes and derivatives thereof, acrylics, natural rubbers, and combinations thereof. Suitable silicone adhesives include, but are not limited to, Dow Corning® 355 available from Dow Corning of Midland, Mich; Dow Corning® X7-2920; Dow Corning® X7-2960; GE 6574 available from General Electric Company of Waterford, N.Y.; and silicone pressure sensitive adhesives, such as those disclosed in U.S. Pat. Nos. 2,857,356, 4,039,707, 4,655,767, 4,898,920, 4,925,671, 5,147,916, 5,162,410, and 5,232,702. Suitable acrylic adhesives include, but are not limited to, vinyl acetate-acrylate multipolymers, including, such as Gelva® 7371, available from Monsanto Company of St. Louis, Mo.; Gelva® 7881; Gelva® 2943; I-780 medical grade adhesive available from Avery Dennison of Painesville, Ohio; and acrylic pressure sensitive adhesives, such as those disclosed in U.S. Pat. Nos. 4,994,267, 5,186,938, 5,573,778, 5,252,334, and 5,780,050.

A removable liner sheet 110 covers the active agent-containing layer 120 and is attached to the adhesive layer 140. The selection of the removable release-liner 110 is dependent on the type of the adhesive in use, and is well known to a person skilled in the art. The release-liner 110 is typically a polymer sheet or a paper coated with a polymer, which have rather weak adhesion toward the adhesive layer 140, therefore allowing itself being easily removed prior to use without damaging the adhesive layer 140.

In addition to or in lieu of the adhesive 140, the apparatus 500 may be fastened to the body surface with an adhesive tape, an elastic band, a band with a buckle (similar to a leather watch band), or a Velcro band or the like.

Alternatively, the active agent unit 100 may be a transdermal patch such as one of those transdermal active agent delivery devices currently in the market. The examples include transdermal patches of fentanyl (Duragesic® by Janssen Pharmaceutical), nitroglycerin (Nitrodisc® by Roberts Pharmaceutical/G. D., Searle; Nitro-Dur® by Schering/Key Pharmaceutical; and Transderm-Nitro® by Ciba-Geneva, and Minitran® by 3M Riker), 17-β-estradiol (Estraderm® by Ciba-Geneva), clonidine (Catapres®-TTS by Boehringer Ingelheim), testosterone (Testoderm® by Alza; and Androderm® by SmithKline Beecham), scopolamine (Transderm-Scop® by Ciba-Geigy), nicotine (Nicoderm® by Marion Merrell Dow; Habitrol® by Ciba-Geigy; Nicotrol® by McNeil Consumer Products; and Prostep® by Lerderle Lab).

Alternatively, the active agent unit 100 may be an iontophoretic, electroporetic, or phonophoretic device such as one of those devices well-known in the art, e.g., as disclosed in U.S. Pat. Nos. 4,927,408, 5,042,975, 5,224,927, 5,344,394, 5,667,491, 4,767,402, and 5,636,632.

The heating unit 200 comprises a heat-generating layer 210 in which heat-generating materials are immobilized, a liquid reservoir 220, and an outer cover 250 under which the heat-generating layer 210 and liquid reservoir 220 are housed. The heat-generating layer 210 comprises a mixture of oxidizable materials (e.g., oxidizable metal powder(s)) and carbon (e.g., activated carbon powder). Examples of oxidizable metal powders include, are but not limited to, iron, aluminum, magnesium, zinc, and a mixture thereof. Other oxidizing material that can be used in the present invention to generate heat include those described in U.S. Pat. No. 4,114,591 (e.g., ferrosoferric oxide, plumboblumbic oxide, trimanganese tetroxide, black copper oxide and manganese dioxide in the form of fine particle). The heat-generating layer 210 should be essentially free of water or moisture prior to use (e.g., during storage).

The oxidation material may be immobilized by various means including but not limited to a water-permeable permeable bag, mesh, non-woven pad or other fabric materials, and binding agents (e.g., polymers) such as cellulose polymers, polyacrylic polymers, polyurethanes, gelatins and gums. Examples of such polymers include hydroxymethylcellulose, hydroxyethylcellulose, hydroxypropylcellulose, cellulose actates, polyvinylvinylidone (PVP), and copolymers of polyacrylic acid and polyacrylates (Carboset®, Carbopol® and Carbomerg®).

The liquid reservoir 220 contains (e.g., an easily rupturable capsule made of a brittle material such as glass or plastic, or a polymer such as polyethylene or polyacrylate) contains water and is fabricated such that upon rupturing, it can either release all of its contents at once to the heat-generating layer or slowly deliver its contents to the heat-generating layer 210 in a pre-determined and controlled manner (e.g., through sealed orifices in a flexible capsule that easily open upon increased pressure). The rupturing may be accomplished by applied pressure from the user. The liquid reservoir 220 may additionally contain hydrogen peroxide.

The heat-generating layer or the liquid reservoir may additionally contain electrolytes (e.g., salts that are placed in the liquid reservoir 220 in the form of an aqueous solution). The electrolytes/salts include, but are not limited to the salts of sodium, potassium, lithium, calcium, iron, magnesium, and aluminum. Examples of electrolytes include, but are not limited to, NaCl, KCl, LiCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

The outer layer 250 is essentially water-impermeable with controlled oxygen permeability. The outer layer 250 may be made of highly oxygen-permeable polymer membranes such as silicone, polyurethane, polyethylene, and polypropylene. It may be of a microporous nature such as an open-cell foam, close-cell foam, or open-cell foam with a water-impermeable polymer layer on one or both side of the membrane. The extent of oxygen permeability of the outer layer 250 is determined by the material it is made of, its thickness, and its porosity. Optional, there may be a removable cover sheet that is essential impermeable to oxygen and water (e.g., moisture). The removable cover sheet must be partially or fully removed to allow the device to heat. The removable cover sheet may have an adhesive coated on one side in order to affix it to the outer layer 250.

In order to use the device 500, the removable liner 110 is peeled off, and the pressure-sensitive adhesive 140 and the active agent-containing layer 120 of the device 500 is affixed to the a barrier membrane (e.g., the skin) of the user. The heating unit 200 is activated by applying a slight pressure on the liquid reservoir 200 to rupture it. The water comes in contact with the heat-generating layer 210 to start the exothermic reaction.

In the case where all of the liquid is release from the liquid reservoir, heating is controlled by the amount of in-coming oxygen through the outer layer 250, whose permeability to oxygen relies on its intrinsic properties (e.g., membrane material, thickness, and porosity). In one embodiment, to have a well-controlled heating process, the removable cover sheet may be removed only partially to limit the amount of oxygen entering the heating unit 200.

Alternatively, the removable cover sheet may be re-used used to completely cover the outer layer to close the oxygen pathway and, thus, stop the heating process. It may later be reopen to re-start the heating process. In this way, the device in the present invention can provide a pulsatile mode of enhanced active agent delivery (e.g., alternating between baseline and heat-assisted delivery).

In the case where the liquid reservoir contains rupturable orifices, the control of the heat generation process may further be determined by controlling the delivery of the water from the liquid reservoir 220 to the heat-generating layer 210. The delivery rate of the liquid can be controlled by the size and number of the aforementioned orifices to provide an enhanced constant rate of active agent delivery.

In another embodiment of the present invention, more than one liquid reservoirs may be present in the device. Each liquid reservoir may be individually ruptured at a predetermined time by the user as needed. An enhanced delivery of active will follow each rupturing of the liquid reservoir agents for a certain period of time, thus, also resulting in a pulsatile delivery profile.

The target temperature range according to the present invention is between about 38° to about 50° C. (e.g., between about 40° C. to 42° C.). The heating period in the present invention may vary dependent on the active agent being delivered and may range from a few minutes to longer than a day. In general, if the heating duration is short (e.g., less than 10 minutes), the operating temperature may be at the higher end of the above temperature range. However, if the heating period is longer, a lower operating temperature (e.g., less than 42° C. is preferred to avoid heat-related tissue injury.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. An exothermic device for topically delivering an active agent, said device comprising:

(a) a plurality of liquid reservoirs, wherein said reservoirs are capsules comprising water;

(b) a heating element, said heating element comprising an oxidizable material and where said heating element is in communication with said liquid reservoir;

(c) an oxygen-permeable outer-layer, wherein said oxygen-permeable layer is in communication with said heating element, permits oxygen from the environment to contact said heating clement, and substantially inhibits the permeation of water from the heating element into the environment;

(d) an active agent; and (e) a water-impermeable layer, wherein said water-impermeable layer separates said heating element and said active agent;

wherein upon the rupturing of said liquid reservoir, said water contacts said heating element and said oxygen to create an exothermic reaction.

2. A device of claim 1, wherein said liquid reservoir is contained between said oxygen-permeable layer and said water-impermeable layer.

3. A device of claim 1, wherein said device further comprises an adhesive layer, said adhesive layer comprising an adhesive for affixing said device to the skin of the user.

4. A device of claim 3, wherein said device further comprises a removable liner affixed to said adhesive layer.

5. A devise of claim 3, wherein said adhesive layer comprises said active agent.

6. A device of claim 1, wherein said liquid reservoir further comprises a salt, said salt selected from the group consisting of NaCl, KCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

7. A device of claim 1, wherein said heating element further comprises a salt, said salt selected from the group consisting of NaCl, KCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

8. A device of claim 1, wherein said oxidizable material comprises carbon and metal powder, said metal powder selected form the group consisting of iron, aluminum, magnesium, zinc, and a mixture thereof.

9. A device of claim 1, wherein said oxidizable material comprises carbon and an inorganic powder, said inorganic powder selected from the group consisting of ferrosoferric oxide, plumboblumbic oxide, trimanganese tetroxide, black copper oxide and manganese dioxide.

10. A device of claim 1, wherein said heating element is contained within a water-permeable membrane.

11. A device of claim 1, wherein said heating clement further comprises a polymer.

12. A device of claim 1, wherein said active agent is for the treatment of acne.

13. A device of claim 1, wherein said oxygen-permeable layer is an open-oell foam.

14. A device of claim 1, wherein said device further comprises a removable oxygen-impermeable cover sheet affixed to said oxygen-permeable layer.

15. A device of claim 1, wherein said exothermic reaction is between about 40° C. and 42° C.

16. A method of topically delivering an active agent to a mammal, said method comprising attaching the device of claim 1 to a barrier membrane of said mammal.

17. A method of claim 16, wherein said mammal is a human.

18. A method of claim 17, wherein said device is attached to the skin of said human.

19. A method of claim 17, wherein said device is attached a mucosal layer of said human.

* * * * *